United States Patent
Lolachi et al.

(10) Patent No.: US 7,473,216 B2
(45) Date of Patent: Jan. 6, 2009

(54) APPARATUS FOR SEPARATION OF A FLUID WITH A SEPARATION CHANNEL HAVING A MIXER COMPONENT

(75) Inventors: Houshang Lolachi, Rockville, MD (US); Ruediger Witt, Strande (DE)

(73) Assignee: Fresenius Hemocare Deutschland GmbH (DE)

( * ) Notice: Subject to any disclaimer, the term of this patent is extended or adjusted under 35 U.S.C. 154(b) by 516 days.

(21) Appl. No.: 11/110,689

(22) Filed: Apr. 21, 2005

(65) Prior Publication Data
US 2006/0240964 A1    Oct. 26, 2006

(51) Int. Cl.
*B04B 5/04*    (2006.01)
(52) U.S. Cl. ........................................ 494/45
(58) Field of Classification Search ............. 494/18, 494/23–30, 38, 41, 43, 45, 47–48, 50, 56; 210/781–782
See application file for complete search history.

(56) References Cited

U.S. PATENT DOCUMENTS

| | | | | |
|---|---|---|---|---|
| 2,661,150 A | * | 12/1953 | Abbott, Jr. | 494/27 |
| 3,096,283 A | * | 7/1963 | Hein | 494/38 |
| 3,239,136 A | * | 3/1966 | Hein | 494/1 |
| 3,244,362 A | * | 4/1966 | Hein | 494/1 |
| 3,244,363 A | * | 4/1966 | Hein | 494/1 |
| 3,456,875 A | * | 7/1969 | Hein | 494/3 |
| 3,675,846 A | * | 7/1972 | Drucker | 494/45 |
| 4,007,871 A | * | 2/1977 | Jones et al. | 494/45 |
| 4,010,894 A | * | 3/1977 | Kellogg et al. | 494/45 |
| 4,330,080 A | | 5/1982 | Mathieu | |
| 4,342,420 A | | 8/1982 | Rosemeier et al. | |
| 4,386,730 A | | 6/1983 | Mulzet | |
| 4,387,848 A | * | 6/1983 | Kellogg et al. | 494/81 |
| 4,447,221 A | * | 5/1984 | Mulzet | 494/45 |
| 4,708,712 A | * | 11/1987 | Mulzet | 494/45 |
| 4,934,995 A | * | 6/1990 | Cullis | 494/45 |
| 5,006,103 A | * | 4/1991 | Bacehowski et al. | 494/45 |

(Continued)

FOREIGN PATENT DOCUMENTS

EP    1 375 006    7/1998

(Continued)

OTHER PUBLICATIONS

PCT International Search Report dated Aug. 10, 2006, with Patent Family Annex, issued in PCT Application No. PCT/US2006/014756.

(Continued)

*Primary Examiner*—Charles E Cooley
(74) *Attorney, Agent, or Firm*—Nixon & Vanderhye PC (57) ABSTRACT

For an effective separation of more than one kind of particle from a mixture, a plurality of separation stages are provided, arranged in series. Mixer elements may be disposed along the flow path to disturb the sedimenting particles, to release entrained lighter particles. Further, the separation channel may widen near the particle recovery port(s), to well suspend lighter particles in the fluid as denser particles are extracted and/or to allow gravitational forces to more effectively influence particle movement. In an example embodiment one stage utilizes Coriolis force in a narrow, radial passage for concentrating and agglomerating particles. The serial separation stages may be communicated with a radially inward extending passage to limit undesirable particle spill-over.

16 Claims, 8 Drawing Sheets

U.S. PATENT DOCUMENTS

| | | | | |
|---|---|---|---|---|
| 5,217,426 | A * | 6/1993 | Bacehowski et al. | 494/45 |
| 5,217,427 | A * | 6/1993 | Cullis | 494/45 |
| 5,651,766 | A * | 7/1997 | Kingsley et al. | 604/6.04 |
| 5,704,889 | A * | 1/1998 | Hlavinka et al. | 494/37 |
| 5,733,253 | A * | 3/1998 | Headley et al. | 604/4.01 |
| 5,759,147 | A * | 6/1998 | Bacehowski et al. | 494/45 |
| 5,792,038 | A * | 8/1998 | Hlavinka | 494/45 |
| 5,876,321 | A * | 3/1999 | Hlavinka et al. | 494/10 |
| 5,904,645 | A | 5/1999 | Hlavinka | |
| 5,906,570 | A * | 5/1999 | Langley et al. | 494/45 |
| 5,913,768 | A * | 6/1999 | Langley et al. | 494/7 |
| 5,954,626 | A | 9/1999 | Hlavinka | |
| 6,019,742 | A * | 2/2000 | Headley et al. | 604/4.01 |
| 6,039,711 | A * | 3/2000 | Headley et al. | 604/4.01 |
| 6,071,422 | A | 6/2000 | Hlavinka et al. | |
| 6,074,335 | A * | 6/2000 | Headley et al. | 494/26 |
| 6,099,491 | A * | 8/2000 | Headley et al. | 604/6.11 |
| 6,277,060 | B1 * | 8/2001 | Neumann | 494/37 |
| 6,334,842 | B1 * | 1/2002 | Hlavinka et al. | 494/36 |
| 6,348,156 | B1 | 2/2002 | Vishnoi et al. | |
| 6,439,577 | B2 * | 8/2002 | Jorgensen et al. | 277/374 |
| 6,514,189 | B1 * | 2/2003 | Hlavinka et al. | 494/37 |
| 6,524,231 | B1 * | 2/2003 | Westberg et al. | 494/43 |
| 6,558,307 | B2 * | 5/2003 | Headley | 494/37 |
| 6,602,179 | B1 * | 8/2003 | Headley et al. | 494/41 |
| 6,613,009 | B1 * | 9/2003 | Bainbridge et al. | 604/6.01 |
| 6,824,506 | B1 * | 11/2004 | Lamphere et al. | 494/41 |
| 6,852,074 | B1 * | 2/2005 | Jorgenson et al. | 494/13 |
| 7,029,430 | B2 * | 4/2006 | Hlavinka et al. | 494/36 |
| 7,094,196 | B2 | 8/2006 | Felt | |
| 7,094,197 | B2 * | 8/2006 | Hlavinka et al. | 494/37 |
| 7,166,217 | B2 * | 1/2007 | Holmes et al. | 210/257.1 |
| 2002/0016244 | A1 | 2/2002 | Unger et al. | |
| 2002/0058575 | A1 * | 5/2002 | Hlavinka et al. | 494/3 |
| 2002/0068674 | A1 | 6/2002 | Hlavinka et al. | |
| 2002/0068675 | A1 | 6/2002 | Felt et al. | |
| 2002/0142909 | A1 * | 10/2002 | Sakota | 494/41 |
| 2003/0166445 | A1 | 9/2003 | Rochat | |
| 2004/0164032 | A1 | 8/2004 | Felt | |
| 2004/0245189 | A1 | 12/2004 | Robinson | |
| 2006/0191857 | A1 * | 8/2006 | Hlavinka et al. | 210/782 |
| 2006/0240964 | A1 * | 10/2006 | Lolachi et al. | 494/37 |

FOREIGN PATENT DOCUMENTS

EP   1281407 A1 *   2/2003

OTHER PUBLICATIONS

PCT International Preliminary Report on Patentability dated Oct. 23, 2007, issued in PCT Application No. PCT/US2006/014756.

PCT International Search Report dated Oct. 11, 2006, issued in PCT Application No. PCT/US2006/014756.

PCT Written Opinion of the International Searching Authorit dated Oct. 11, 2006, issued in PCT Application No. PCT/US2006/014756.

Sugai; Fresenius AS.TEC204 Blood Bell Separator; Therapeutic Apheresis and Dialysis 7(1): XP009069496; pp. 37-43; 2003.

* cited by examiner

APPARATUS FOR SEPARATION OF A FLUID WITH A SEPARATION CHANNEL HAVING A MIXER COMPONENT

FIELD OF THE INVENTION

The invention pertains to the separation of particles suspended in fluids using centrifugation.

BACKGROUND OF THE INVENTION

For the treatment of certain diseases or deficiencies, blood components such as red blood cells, platelets, and plasma are needed. According to regulations in nearly all countries, these blood components have to be provided in standard therapeutic quantities and qualities. A standard therapeutic quantity of red blood cells can be prepared from a unit (pint) of whole blood collected from a single donor, whereas to prepare a standard therapeutic quantity of platelets, it is necessary to combine platelets from several discrete whole blood donations. As these platelets originate from different donors, it is a requirement that only platelets from donors whose blood group types are closely matched be mixed.

As an alternative, a cell separation device can be used, which can continuously extract the platelets from the blood of a single donor, who is connected to the machine via a tubing set. From the incoming blood being processed within the machine, the platelets are extracted and collected in a storage container, whereas, typically, the remaining part of the blood is returned to the donor.

Blood banks, the main users of these machines, are under cost pressure and are looking more and more for faster and more efficient ways of producing blood products. This has led to the development of machines that draw the blood with higher and higher flow volumes, which often causes discomfort to the donors and even may exclude donors with limited vein capacity from donating with such devices. On the other hand, blood banks need to increase their pool of donors because of the rising need for blood products, sometimes causing severe blood shortages, especially during the summer-time and holidays.

A solution to these problems would be a significant increase in separation efficiency of the cell-separation machines, especially for platelets, because this would lead to a significant reduction in donation time without the need to exclude traditional donors with limited vein capacity.

SUMMARY OF THE INVENTION

Difference in density is the main differentiating factor used by the centrifuges of conventional cell separators to separate and collect different kinds of particles. These devices have reached a level of efficiency which has not changed very much for many years. This is mainly due to the difficulty of efficiently extracting and separating platelets from plasma, due to the fact that both fractions have nearly the same densities.

For an effective separation of more than one kind of particle from a solution comprising a mixture of particles, more than one separation stage, arranged in series, is provided according to the invention. Each stage can then be optimised for each kind of target particle.

Thus, in the following description a multi-stage centrifugal separation geometry is proposed as an embodiment of the invention. In the disclosed embodiments, whole blood is used as an example of a fluid containing mixed suspended particles intended to be separated into separate components, including but not limited to, erythrocytes (red blood cells), thrombocytes (platelets), and platelet poor plasma.

Conventional cell separation chambers essentially rely on gravity produced by centrifugation, alone, for blood component separation. That is, under the influence of gravitational force, created in a centrifuge, fluid-suspended particles start to move in the direction of the gravitational force with different velocities, mainly depending on their densities and size. A limitation of such conventional apparatuses, however, is that separation dependent substantially solely on gravitational forces results in entrainment of lighter particles with sedimented heavier particles and escape of target particles with the fluid component. In an embodiment of the invention, a combination of forces and flow conditions are utilized, in addition to the traditional gravitational force, to enhance separation of components for maximum efficiency.

In an example embodiment of the invention, a blood separator/centrifuge is provided that incorporates a plurality of mixer elements that facilitate the separation of platelets by disturbing the separated fluid component (e.g., plasma) to disturb a buffy coat forming above the denser sedimented particles (e.g., red blood cells) to in turn release additional lighter particles (e.g., platelets) from the red blood cells below the buffy coat.

According to a further feature that may be incorporated in an example embodiment of the invention, the primary separation channel widens near the red blood cell recovery port, to break up the buffy coat, due to the high plasma velocity adjacent the divergence, so that red blood cells remain together and platelets are well suspended in the plasma.

According to a further feature that may be included in an example embodiment of the invention, from the widened chamber, platelet rich plasma enters a part serpentine channel that extends radially inwardly, against centrifugal forces, to effectively define a filter whereby heavier red blood cells and white blood cells are separated as heavier particles. Further along, the serpentine flow path is reversed so as to be radially outward where the flow experiences Coriolis Force to separate and agglomerate platelets. Thereafter the flow is to a divergent zone for further separation of platelets.

Thus, the invention may be embodied in a centrifuge assembly for separating particles of differing density from a fluid mixture of particles comprising: a base component disposed for rotation about a central axis thereof and including an inlet for said mixture, a first particle outlet for a first particle type having a first density, a fluid outlet for fluid from which said first particle type has been substantially removed, and a first channel extending from said mixture inlet to said first outlet, said first channel being defined by a radially inner side wall, a radially outer side wall, a channel bottom wall, and a top cover (not shown), the radially inner side wall being radially closer than the outer side wall to an axis of rotation of the base component; wherein at least a part of said first channel extends in an arc proximate an outer peripheral edge of said base component; and at least one mixer component is disposed to project into said first channel from one of said walls thereof, so that as said first particles are separated from said mixture while said base component is rotating and as said mixture flows along said first channel, said at least one mixer component re-mixes at least some of said separated first particles.

The invention may also be embodied in a centrifuge assembly for separating at least first and second particle types having different densities from a fluid mixture of at least said first and second particle types suspended in a fluid comprising: a base component having a generally circular shape and defining a path for fluid extending generally in a circumferential direction thereof, wherein said path for fluid is defined in first and second part circumferential stages, and further comprising a generally radial passage communicating a second, terminal end of said first stage and a first, beginning end of said second stage, wherein said first end of said second stage is disposed radially inwardly of said second end of said first stage.

The invention may also be embodied in a centrifuge apparatus for separating particles from a mixture of fluid and at least said particles comprising: a generally circular base for being rotated in a first direction about a central axis thereof for generating forces to facilitate separation of said particles from said mixture and a channel extending at least part circumferentially of said base, said channel having an inlet for said mixture, a particle outlet, and a fluid outlet for fluid from which said particles have been substantially removed, said inlet being disposed proximate said center of said base, said channel including a first portion extending radially outwardly from said inlet, a second portion extending part circumferentially of said base proximate an outer periphery of said base to a vicinity of said particle outlet, and a third portion extending at least one of part circumferentially and radially inwardly of said base from a vicinity of said particle outlet to said fluid outlet, wherein particles in said mixture flowing along said first portion experience Coriolis forces for urging said particles towards a downstream outer wall thereof, and particles in said mixture flowing along said second portion experience gravitational forces for urging said particles towards a radially outer wall thereof.

The invention may additionally be embodied in a method for separating a cell suspension into desired component particle fractions, comprising the steps of: introducing the cell suspension in a separation channel of a separation chamber; rotating the separation chamber about an axis of rotation thus forcing the cell suspension to distribute in the separation channel along a path extending from a cell suspension inlet to a fluid outlet; disturbing sedimenting particles, to release lighter particles entrained in said sedimenting particles and/or to re-mix sedimenting particles in the flowing fluid component at at least one point along the length of said separation channel; and withdrawing the desired component fractions at corresponding outlets along the separation channel.

BRIEF DESCRIPTION OF THE DRAWINGS

These and other objects and advantages of this invention, will be more completely understood and appreciated by careful study of the following more detailed description of the presently preferred example embodiments of the invention taken in conjunction with the accompanying drawings, in which.

DETAILED DESCRIPTION OF EXAMPLE EMBODIMENTS

A blood separator/centrifuge embodying the invention is comprised of a base plate that defines at least one channel for blood or blood components. In a conventional manner, a cover plate (not shown) is rigidly connected to seal the blood channel. If deemed necessary or desirable, a portion of the blood channel may be defined in the cover plate, although more typically the cover plate will be generally planar serving substantially only a blood channel sealing function. A central opening C is defined to extend through the base component and through the cover plate (not shown) and is used for securing the cell separator in a centrifuge unit.

As illustrated variously in FIGS. 1, 4, 6, 8, and 9, the base 10, 110, 210, 310, 410 is in the form of a disk of circular geometry and comprises molded formations and/or inserts to define blood component channels, ducts and ports as described in greater detail below. In an exemplary embodiment, the base is made as an injection molded unit from a suitable synthetic material, although parts thereof may be defined from other biocompatible materials including metals. As noted above, the base defines with the cover a housing having a rotation axis extending through the central hole. After insertion into a centrifuge, the cell separator is driven to rotate, in a counter-clockwise direction in the described example embodiments but not limited to counter-clockwise only.

As noted, several examples of particle separation devices embodying the invention are described hereinbelow. Corresponding components of the various embodiments are labelled in the various figures with like reference numbers respectively incremented by 100. To simplify the disclosure, however, a description of the corresponding components may be omitted or limited to variant details.

Figure 1:
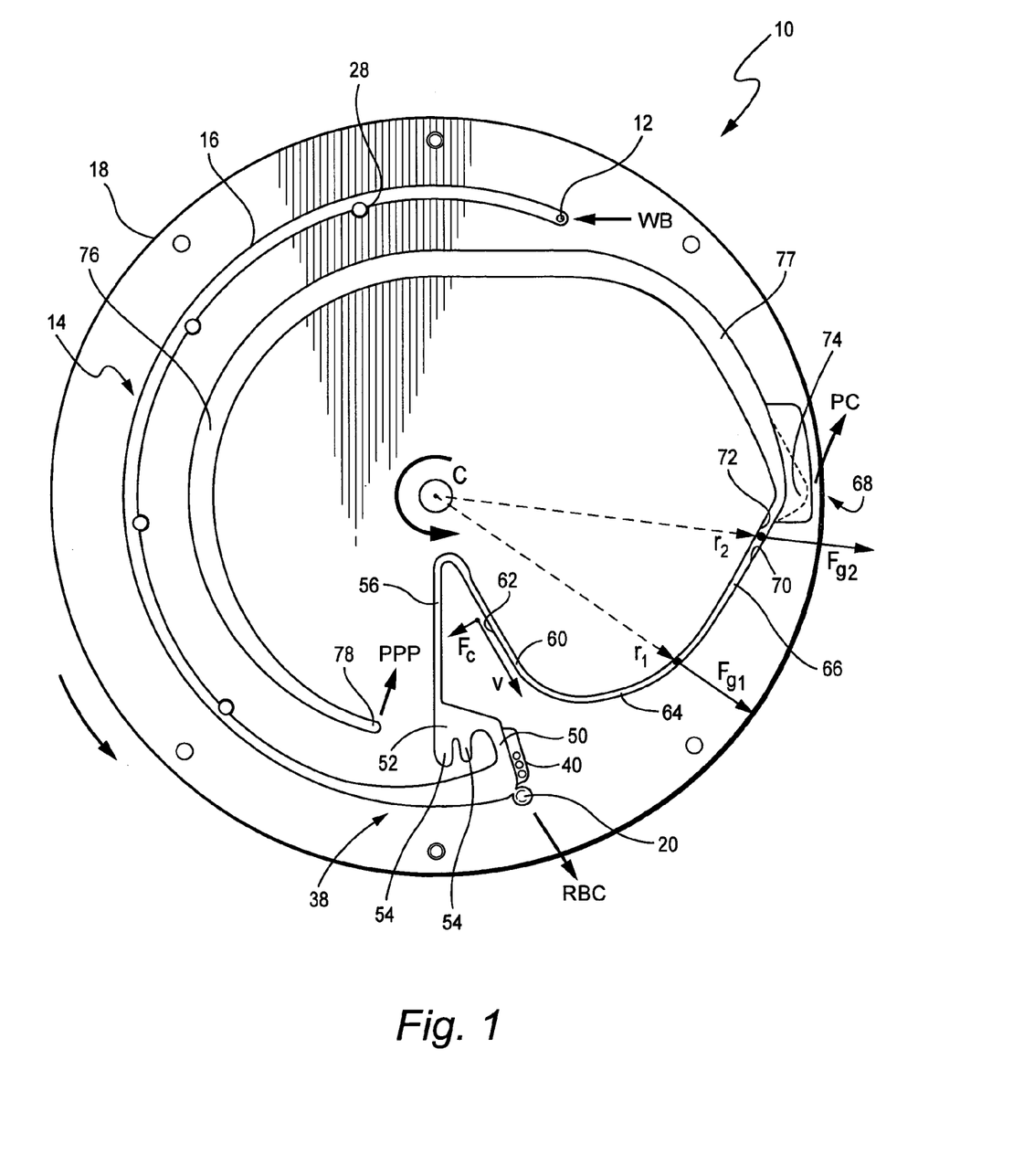
FIG. 1 is a schematic plan view of a rotary particle separation chamber with a first separation stage and a second separation stage in sequence as an example embodiment of the invention.

Referring to FIG. 1, whole blood (WB) is received through port 12 of a first stage 14 of the blood channel of the base 10 of the separation housing. This first stage 14 provides a blood channel 16 that extends generally in the direction of rotation along at least about one-half, more preferably between about 50%-75% (180°-270°) of the circumference of the disk shaped base 10, close to the radially outer edge 18 of the base. The long channel 16 is provided so that maximum hematocrit is formed before the red blood cells exit at red blood cell port 20. A packing factor, which results mainly from the amount of centrifugal gravitational force $F_g$ to which a fluid-volume-element of whole blood is exposed to during the time $T_g$ during which it moves from the input port 12 to red blood cell port 20 at the end of first stage 14, is mainly responsible for the separation result at the end of the first stage. The long path of the blood channel 16 of the first stage 14 can be used to produce a high hematocrit of the extracted RBCs by controlling time $T_g$ to be appropriately long, by using a low flow rate, or, to cut down on the length of the entire donation procedure, by using high flow rates while still providing standard values of hematocrit in the RBC fraction extracted at RBC port 20.

Thus, as whole blood passes to and along the first stage channel 16, due to gravitational rotational force, the heavier red blood cells 22 (FIG. 2) begin to separate from the lighter particles and plasma. The goal is to isolate as much of the red blood cells as possible while reserving as much of the platelets as possible. However, as the heavier particles sediment to the outer wall 24 of channel 16, they entrap part of the lighter particles, such as platelets, in the sediment. Meanwhile, a buffy coat 26 containing most of the cells which are not as dense as red blood cells, such as leucocytes, monocytes, stem cells, granulocytes and platelets, forms above the sedimented red blood cells. This hinders further retrieval of trapped platelets from the sediment.

The efficiency of platelet extraction of conventional cell separators at the first stage has levelled out at about 80%. That is, as red blood cells (red blood cell concentrate) is sedimented quickly and effectively, it drags and traps 20% or more of the platelets. Therefore, these platelets are not available to enter a second separation stage as part of platelet rich plasma.

In an example embodiment of the invention, at least one mixer or mixer element is used in order to remix at least a portion of the sedimented red blood cell concentrate and in doing so release some of the platelets back into the fluid stream to enter the platelet rich plasma portion of the separation. The intended mixing effect can be achieved by various kinds of arrangements, preferably by smooth non vortex creating modifications of the inner wall such as hydrofoil profiles, or rows of bars or cylinders, or Rankin-shape columns, all preferably shaped in such a way as to avoid the forming of vortices and positioned away from the area populated by red blood cells to avoid damage to these cells. The number, shape, and relative positions of the mixer elements is determined based on the goal to achieve optimal remixing of plasma and red blood cells without disturbing the separation process too much, e.g., avoid development of vortices. As more platelets become available in the platelet rich plasma, the overall efficiency of platelet collection is increased.

In the illustrated example embodiments, a plurality of mixer elements 28 are provided and disposed at spaced positions along the first stage channel to project into the channel from a wall thereof. The mixer elements may be provided as a mixer component that is received in a corresponding receptacle in, e.g., the inner wall of the first stage channel, from which it projects into the channel. In the alternative, the mixer elements may be disposed or defined on the surface of the channel wall.

Figure 2:
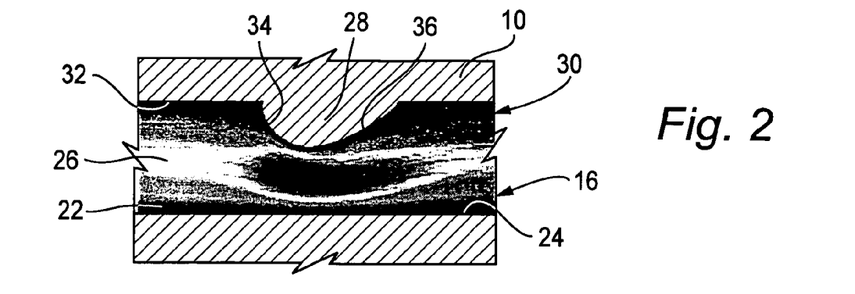
FIG. 2 is a schematic cross-sectional view illustrating a mixer element embodying the invention for disrupting the forming buffy coat layer.
Figure 3A:
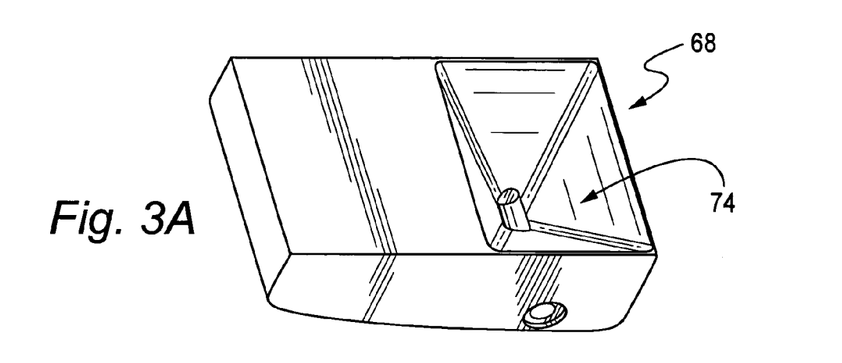
FIGS. 3A-3D schematically illustrates a platelet concentrate extraction port according to one example embodiment.
Figure 3B:
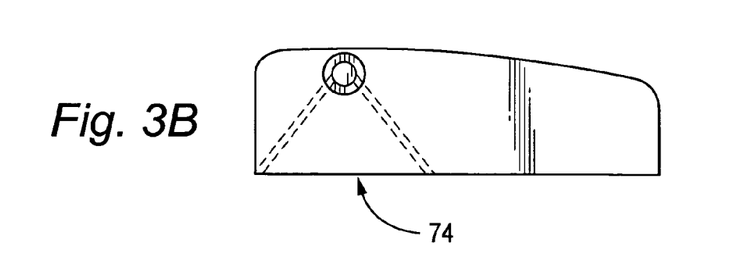
Figure 3C:
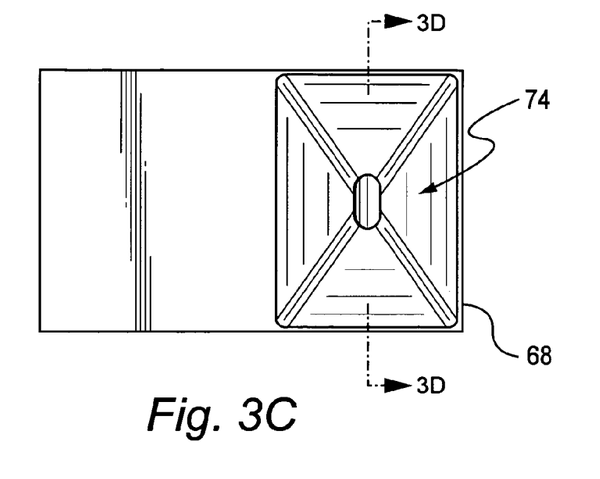
Figure 3D:
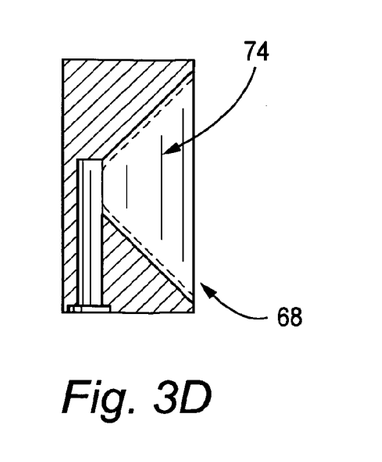
Figure 4:
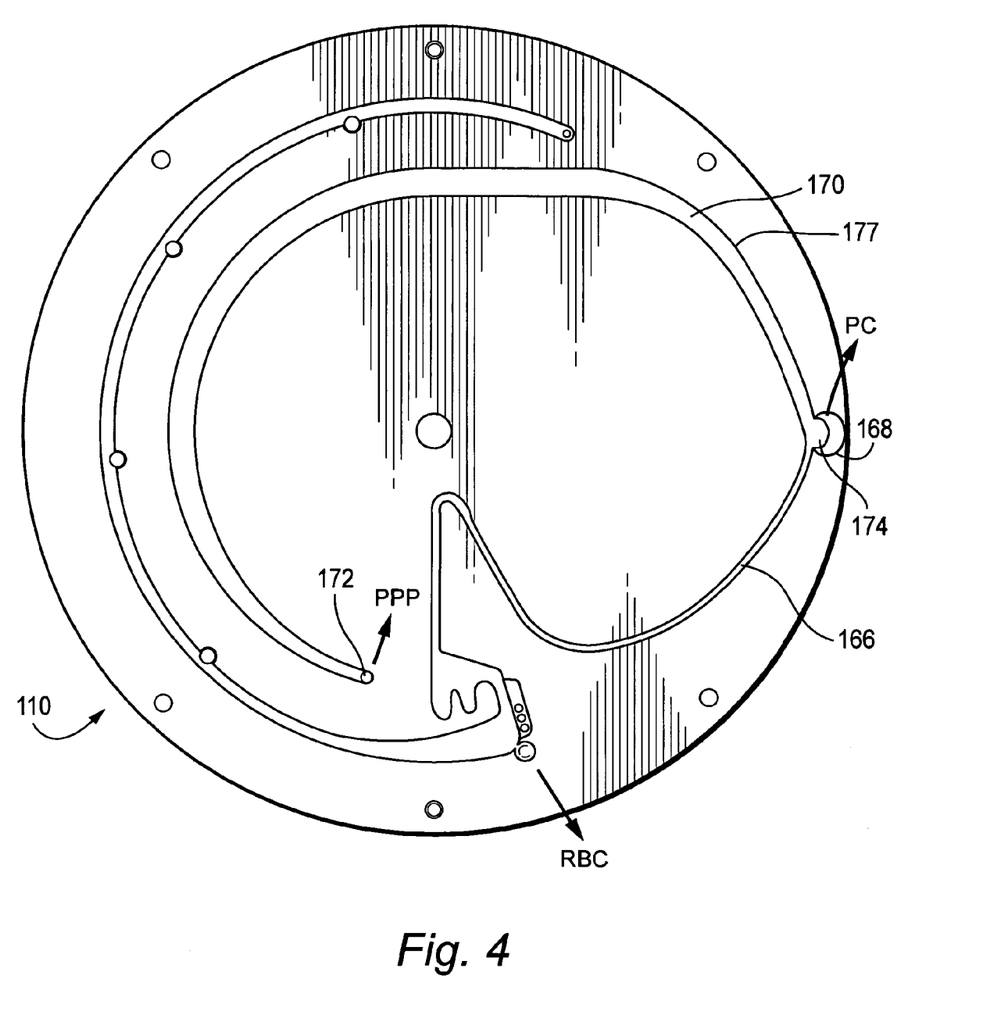
FIG. 4 is a schematic plan view of another example embodiment, having an alternate platelet concentrate extraction port.
Figure 5A:
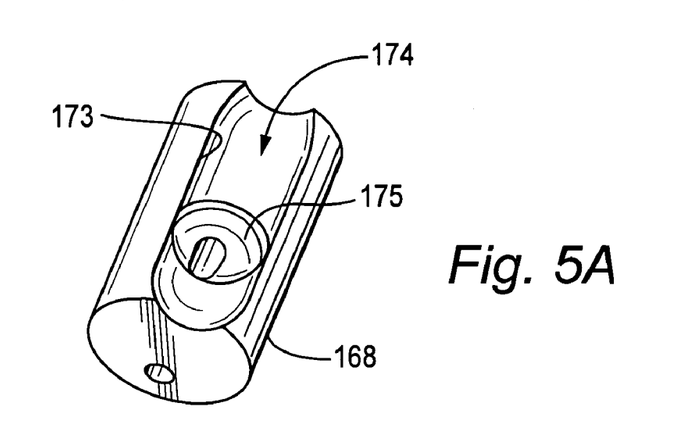
FIG. 5A-5D illustrate in greater detail the platelet concentrate extraction port of FIG. 4.
Figure 5B:
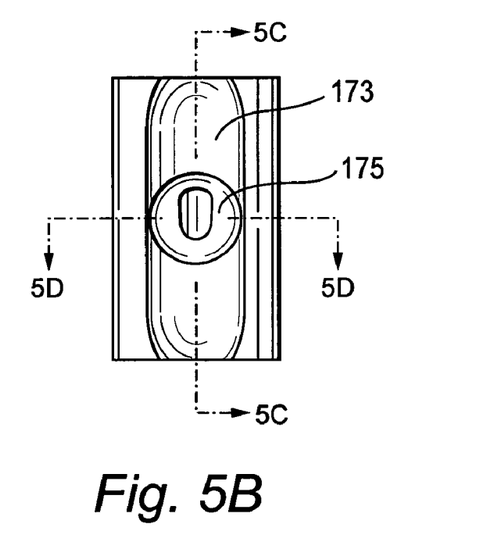
Figure 5C:
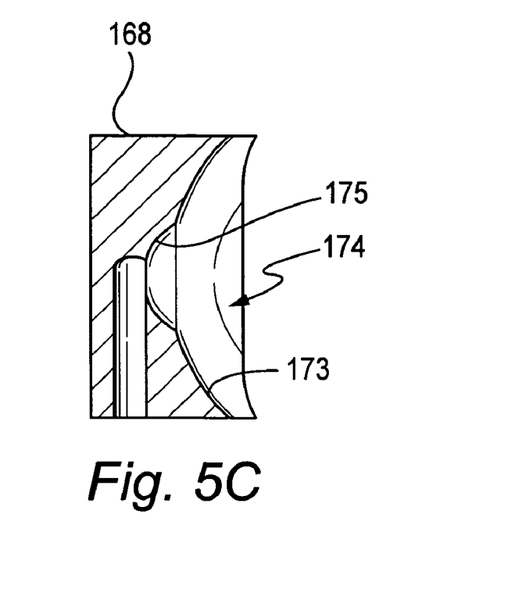
Figure 5D:
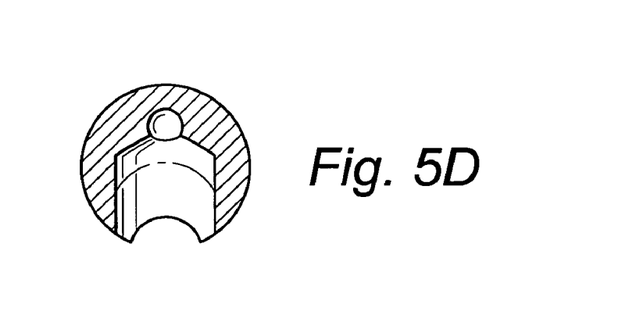

FIG. 2 is a schematic cross-sectional view of an example configuration of a mixer element 28. In this example, the mixer element is disposed to protrude from the channel inner wall 32 into the flowing blood products to make the flow turbulent, so as to break up the forming buffy coat 26 so that the lighter, potentially trapped cells such as platelets are released back into the plasma area 30 and buffy coat 26 from the compacted red blood cells 22. While these mixing elements or turbulators may take on a variety of forms including a plate like protrusion, in a presently preferred embodiment the mixer element 28 has a curved outer surface so as to provide for a controlled disturbance to the flow and so as to avoid risk of damage to the blood components. In the embodiment illustrated in FIG. 2, the mixer element 28 has a hydrodynamic formation including a rounded leading edge 34 and an inclined trailing edge 36.

Thus, the mixers interrupt and modulate the flow pattern and partially remix the sedimented red blood cells. By positioning the mixers on the inner wall 32 of the channel 16 (as opposed to the outer wall 24) additional stress induced by these partial obstacles on the flowing fluid-suspended cells is minimized. The mixers are discontinued near where the final red blood cells sedimentation is desired, so that the so-called buffy coat at the interface between red blood cells and plasma can be formed. Thus, in the illustrated embodiment, the final mixing element is disposed sufficiently upstream of a diverging portion 38 of the flow path (described in greater detail below) for the buffy coat 26 to form. In this manner, a maximum number of platelets are put back into the space between the high hematocrit red blood cell concentrate 22 and wall 32, while the so-called buffy coat 26 is formed between the final mixing element 28 and the diverging portion 38 of the passage 16.

As noted above, in the illustrated embodiment, a diverging section 38 is provided proximate the end of the first stage 14. By way of example, the elongated channel 16 of the first stage 14 may have a depth on the order of about 3 cm and a width of about 4 mm. Then, in the diverging section 38, the channel widens to 8 or 9 mm or perhaps as much as about 12 mm. In the illustrated embodiment, the blood channel diverges along the final 10-15% of its length. In this example, furthermore, the diverging section 38 has a generally constant radius outer wall and an inner wall tapered in a radially inward direction. The effect of a diverging shaped section is to create a flow velocity distribution such that, under the influence of the flow pattern within this diverging section, the top portion of the buffy coat 26, which contains a high concentration of platelets, distributes into the plasma above it. Meanwhile, the RBC port 20 is placed in such a way along the radially outer wall of the blood channel as to collect red blood cells and other heavier cells, such as white blood cells. The red blood cells and white blood cells, generally mixed with the platelet poor plasma, may be returned to the donor or be collected for red blood cell infusion to a patient.

Depending on the specific properties of the blood or other fluid being separated, which may change over the course of the separation procedure, a position of the buffy coat 26 within the respective flow pattern may vary. Thus, as it is desirable to achieve optimal separation efficiency of the first stage, an adjustment of the position of the buffy coat may be desirable. This adjustment of the interface position can be effected by proper control of the RBC flow rate as a function of whole blood (WB) flow rate and hematocrit. In an example embodiment, an optical sensor 40 is provided to monitor the location of the buffy coat, i.e. the position of the separated particles, more particularly the separation between the buffy coat and the red blood cells. In the event the optical sensor detects that the location or position of the buffy coat/separated particles has shifted from a determined or prescribed optimum position, the inflow of whole blood (WB) may be increased or decreased, or maintained unchanged while the red blood cell removal through port 20 can be accelerated or decelerated, thereby to in effect feedback control of the location of the buffy coat.

With RBC being extracted from port 20, highly enriched plasma, or platelet rich plasma (PRP) containing most of the platelets, enters conduit 50 on its way to the second stage of the separation device. In this regard, as noted above, the flow of plasma above the buffy coat with high velocity causes the break up of the buffy coat and effectively creates the platelet rich plasma that is then transferred to the second stage for further concentration and collection.

Based on actual experiments with blood and using an example embodiment having the above improvements, i.e., at least one mixer element, a blood channel that diverges to disrupt the buffy coat, and using interface location/posiition control, efficiencies of 90% or better have been achieved in regard to platelet extraction for the first stage. That is not to say, however, that all the foregoing improvements must necessarily be provided. Indeed, improved platelet extraction for the first stage may be expected with any one of the noted improvements or various combinations thereof.

In an example embodiment of the invention, the separator is comprised of two separate stages. One stage, as described above, is provided for the separation of platelet rich plasma from red blood cells. The second stage is effectively completely separated from the first stage. An advantage of this is that spill over from the first stage to the second stage, meaning red blood cells spilling over into the second stage is minimized and, further, it is possible to provide traps between the first and second stages in order to trap unwanted cells such as white blood cells and red blood cells. More particularly, the platelet rich plasma flows into and through a radial passage 50 which can be narrower than the blood channel 16 of the first stage. Then, as platelet rich plasma (PRP) passes through segment 52, it experiences a slow down in the flow velocity, due to an increase in the cross-sectional area as shown. This allows the heavier particles or cells, such as red and white cells which to a minor degree are also extracted from the buffy coat, to be trapped in serpentine traps 54. Then, as the platelet rich plasma is exiting the first stage it enters a channel 56 extending radially inward, towards the center of rotation, close to which it then enters the second stage. In the illustrated embodiment, channel 56 ends at a point that is at least about 80-90% of the distance from the outer wall 24 of channel 16 to the center C of the disk. This geometrical configuration of transporting platelet rich plasma from an area of high gravitational force against the gravitational (centrifugal) force towards the center of rotation provides the possibility of configuring the channel in such a way that heavier particles are trapped and cleaned off while the less contaminated PRP continues on through radial conduit 56. The flow against the direction of gravitational force in radial conduit 56 will further prevent the undesired blood cells from entering the second stage, resulting in even cleaner PRP entering the next, Coriolis channel 60, described hereinbelow. It is proposed that the channel depth be maintained generally constant in the region of passages 50, 52 and trap(s) 54. Along passage 56, the depth may be varied if determined to be necessary or desirable to make it shallower or deeper towards the center C.

Figure 6:
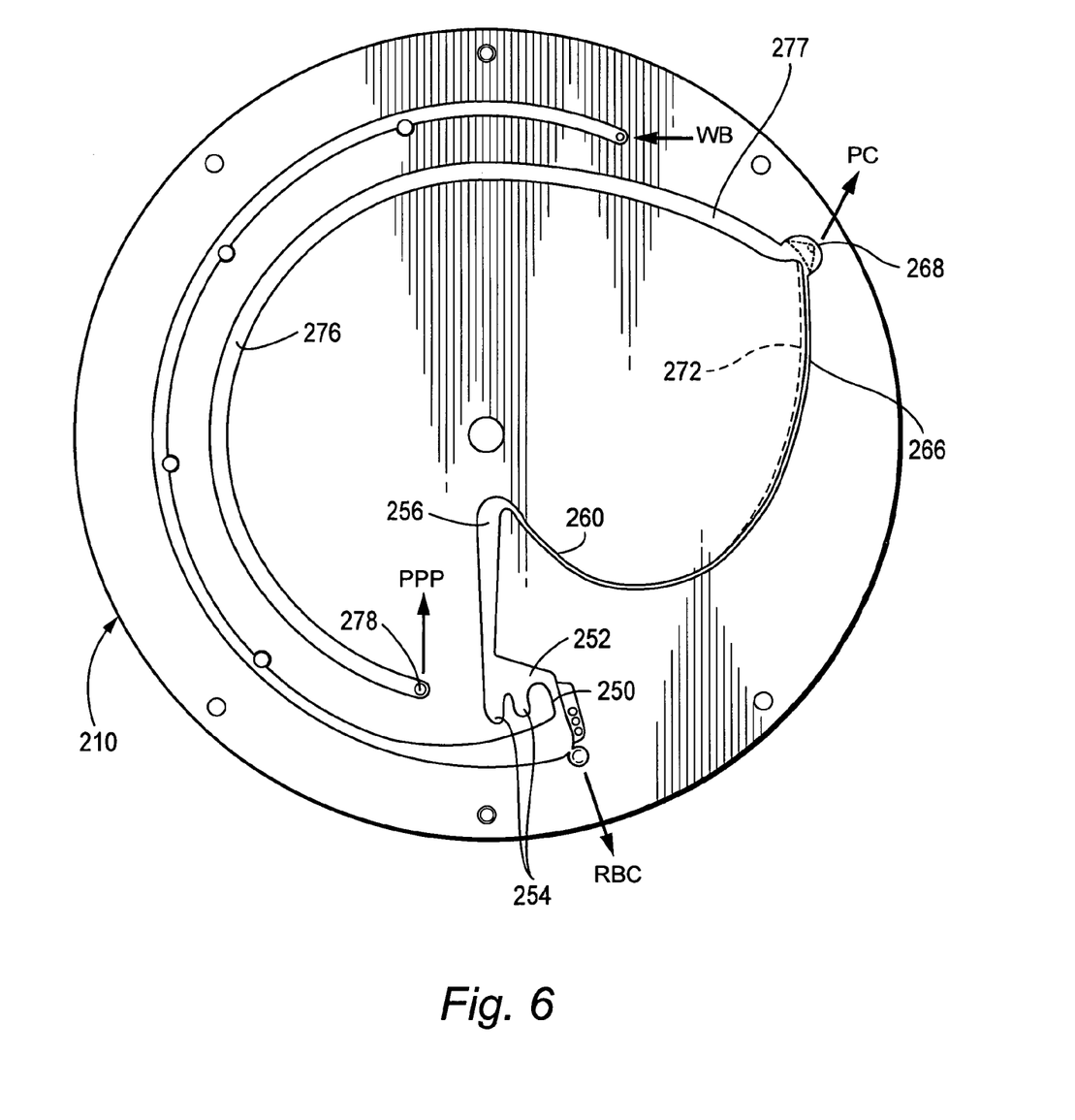
FIG. 6 is a schematic plan view of a further example embodiment of the invention having a modified second stage.

Another embodiment which has been tested successfully is shown in FIG. 6. Here, where PRP (platelet rich plasma) leaves the first stage at 250,252 and flows against gravity through conduit 256. The conduit 256 is designed with an increasing cross sectional area as the PRP flows towards the central axis (as shown in FIG. 6), thus slowing down the flow velocities so that heavy cells such as WBC (white blood cells) can be trapped. The combination of traps 254 with conduit 256 of increasing cross-sectional area enables an efficient technique to clean the PRP from WBC on its way to the second stage.

Referring again to the FIG. 1 embodiment, the platelet rich plasma enters the second stage (the inlet thereto) at a point close to (proximate) the center C of the base plate. The flow in the second stage commences near the center and extends radially outward therefrom to commence separation of platelets due to Coriolis Force.

Coriolis force is defined as $F_c=2\omega v$, where v=flow velocity of the fluid and $\omega$=rotational speed of the centrifuge.

The Coriolis force pushes the platelets toward the outer wall 62 (clockwise in the Figures) thus to separate platelets from the plasma in this narrow chamber/passage. In the illustrated embodiment, the Coriolis channel 60 has a substantially radial geometry with appropriate channel width, e.g. about 1-4 mm, preferably about 2 mm, is used to maximize "v", together with a close to 90 degree angle between v and $\omega$.

It is important to notice that $F_c$ is effective immediately as platelet rich plasma enters channel 60, close to the center C of rotation, since both v and $\omega$ are independent of the distance from the axis of rotation (radius).

As the particles or cells pass through the radial, Coriolis channel 60, they sediment on the outer wall 62 of the channel. Although Coriolis force here is smaller than normal (centrifugal) gravity, the small width of the channel plays an effective role for particles to sediment to the outer wall 62.

Using traditional gravitational force $F_g$:
$F_g=r\omega^2$, where r=radial distance from the axis of rotation, and $\omega$=the rotational speed of the chamber. Thus, the platelets are further continuously concentrated in gravitational segments 64 and 66. By the time the flow arrives at the passage portion 64 and 66, where the centrifugal forces dominate, there is already significant separation and aggregation of the platelets. The coagulates of platelets are heavier and thus more responsive to the centrifugal forces in passages 64 and 66, through which they are directly channelled to the platelet collection port 68. In an example embodiment, the width of channels 64 and 66 ranges preferably between about 1 and 4 mm. Further, the geometry of channel 66 may be straight (as shown in FIG. 1), or may be more curved (as in FIG. 4) in such a way that there is a continuous change of direction on the way from path 60 towards platelet collection port 68. On the other hand, the Coriolis segment is advantageously narrow, e.g., on the order of 2 mm wide so that the platelets do not have long to travel to the channel wall for agglomeration which makes the platelets more susceptible to the gravitational forces in the gravitational segments 64 and 66.

With a Coriolis channel followed by a gravitational channel substantially as described, platelets have been observed to be highly concentrated close to the outer wall 70 of the channel when reaching the end of the gravitational channel segment in a vicinity of the platelet collection port. Thus, as platelet concentrate exits channel 66, there is a highly concentrated stream of platelets flowing on the outer wall 70 of the channel, with clear plasma closer to the inner wall 72 of the channel. However, the velocity with which this stream is flowing is relatively high, since channel 66 is relatively narrow in cross-sectional area. Therefore, according to a further feature that may be advantageously implemented here is to slow down the platelet concentrate stream and allow the gravitational force to gain dominating influence on the platelets, forcing them in the direction of platelet concentrate port 68 where the gravitational force reaches its maximum. This alternative is schematically illustrated in FIG. 6, where the widening of channel 266 is indicated by dotted line 272. Thus, the width of the gravitational segment 66, 166, 266, 366, 466 can be adjusted to create flow characteristics complimentary to the gravitational forces experienced by the fluid and suspended particles. With platelet movement being enhanced and supported by proper shape and contour of the platelet concentrate port, platelets can be continuously harvested in a highly concentrated form through port 68. In the usual case, the concentrated platelets flow out of the platelet concentrate port and are collected in a platelet bag.

FIGS. 3A-3D illustrate a first example embodiment of a platelet extraction port. In this embodiment, the port is disposed substantially mid-height of passage 66 and consists of a quadruple sloped trough well 74 which forces the cells to exit through the collection opening. This well is directly experiencing the high gravitational force produced by centrifugation at this radial location of the second stage. FIGS. 4 and 5A-5D illustrate an alternate platelet extraction port, defined as a substantially cylindrical insert 168 having a well 174 comprised of a part cylindrical portion 173, and a part spherical portion 175, to intercept the platelets and direct them to the outlet for collection.

As platelet concentrate (PC) is extracted at the PC port 68, 168, 268, the fluid remaining, referred to as platelet poor plasma (PPP), continues towards the platelet poor plasma exit. In an example embodiment of the invention (FIGS. 1, 4, and 6), a long path 76, 176, 276 is defined between the platelet concentrate (PC) extraction port 68, 168, 268 and the platelet poor plasma (PPP) exit 78, 178, 278 so that the platelet poor plasma can be effectively cleaned of platelets and white blood cells.

Figure 7:
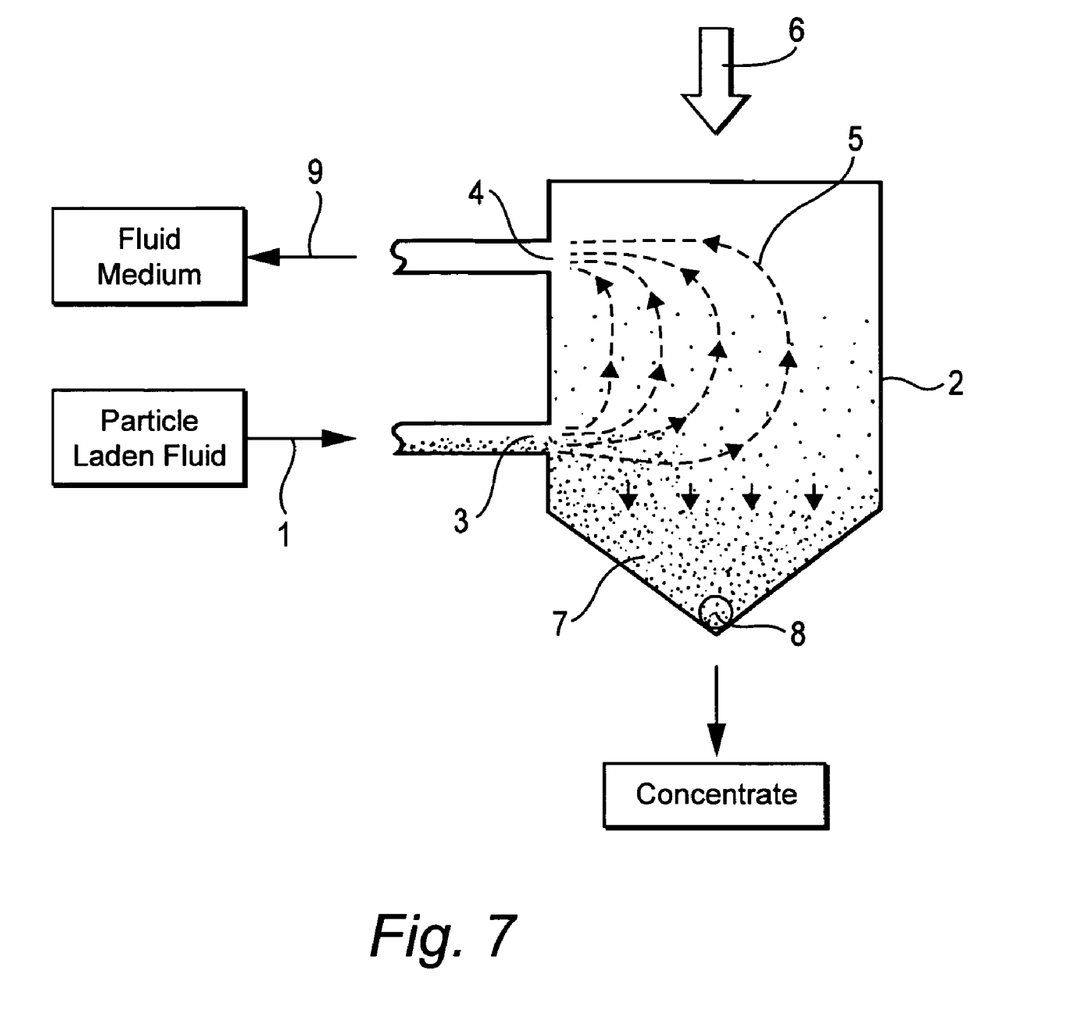
FIG. 7 schematically illustrates the concept of a U-turn for particle precipitation.

FIG. 7 schematically illustrates the conceptional idea and underlying principle of a U-turn approach for particle separation. The incoming flow 1 enters a segment of increased volume 2, with the larger cross sectional area reducing the velocity of the fluid as it moves from input opening 3 towards the exit opening 4, which is located so that flow theretoward is in a direction opposite the direction of the gravitational force at the same time. The geometric arrangement provides for a sharp change in flow direction (U-turn) together with a slowing down of the flow velocity and a forced movement in the direction of gravitational force. Properly combining these measures provides for the intended effect that particles being carried by the fluid are released from following the stream lines 5 of the fluid and, under the influence of the gravitational force 6, start moving towards a collection area 7, the shape of which provides for an effective collection and harvesting of the particles through the particle exit port 8. The exit flow 9, which consists of the fluid without the particle load, leaves through the fluid exit opening 4.

Figure 8:
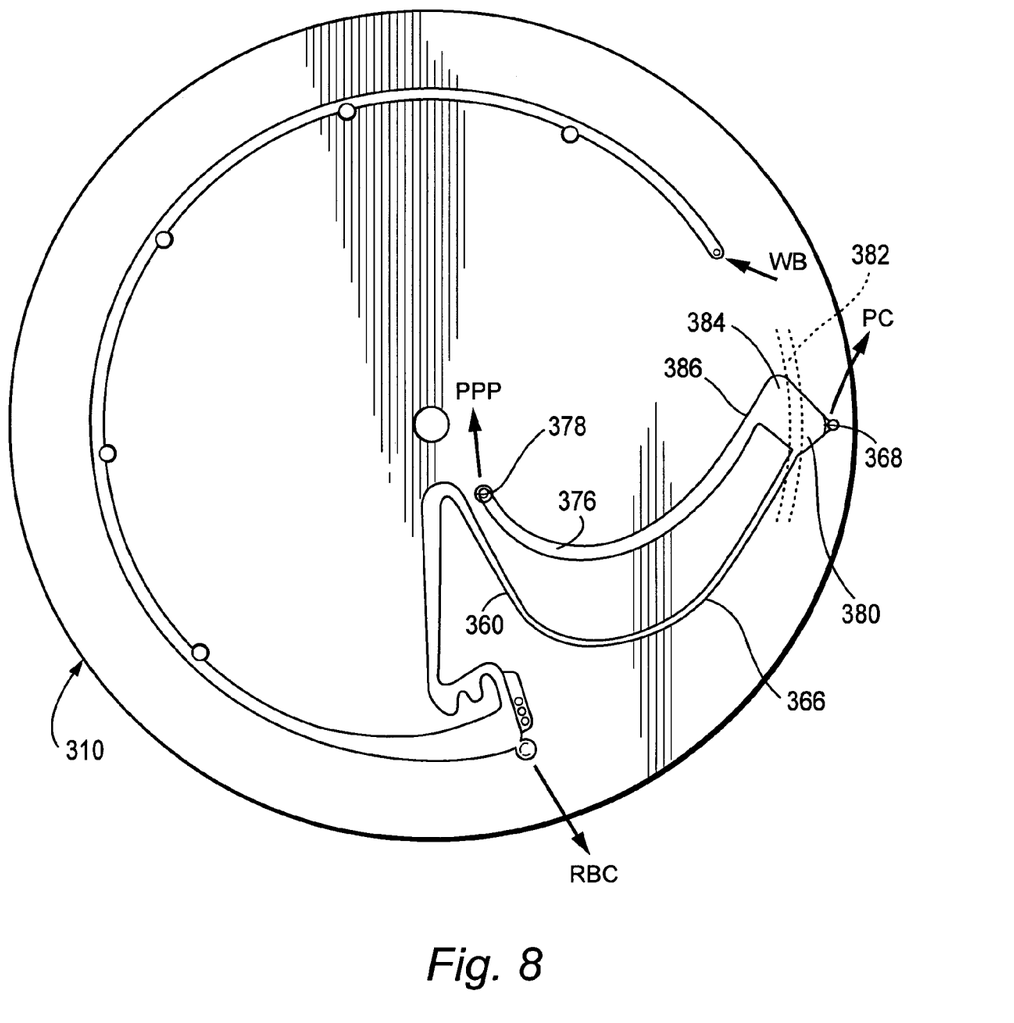
FIG. 8 illustrates an implementation of a "U-turn" concept according to a further example embodiment of the invention.

An example embodiment of the invention adopting the above U-turn approach is depicted in FIG. 8. Here, as the platelet concentrate stream reaches the end of channel 366, it experiences a channel expansion at 380 and the particles or cells slow down and are guided towards the platelet collection port 368. Meanwhile, the cells that were not pulled down sufficiently will fall under the strong influence of the iso-potential lines 382, where the cross-sectional areas are further expanded. In this area the gravitational force tends to further sediment and separate the cells from the plasma, which itself is forced upward into section 384 leading to a complete U-turn at 386. Therefore, cells that have not been captured initially have to go past the iso-potential lines 382 in a flow direction against gravity and make a U-turn. The above transition will also greatly increase the probability of cell to cell interaction making small aggregates so that they will become heavier and drop downward. Therefore, the U-turn slows down the flow velocity, changes the flow direction, and promotes platelet interaction for aggregation, all of which contribute to a highly efficient sedimentation towards the platelet collection port 368.

Thus, the Coriolis force is advantageously used in passage 360 for preliminary separation of the platelets, followed by centrifugal separation in passage 366 and platelet collection at 368. The provision of the U-turn and channeling facilitates agglomeration and platelet drop. The volume change at 380 also provides for flow reduction for platelet collection due to gravitational forces.

Figure 9:
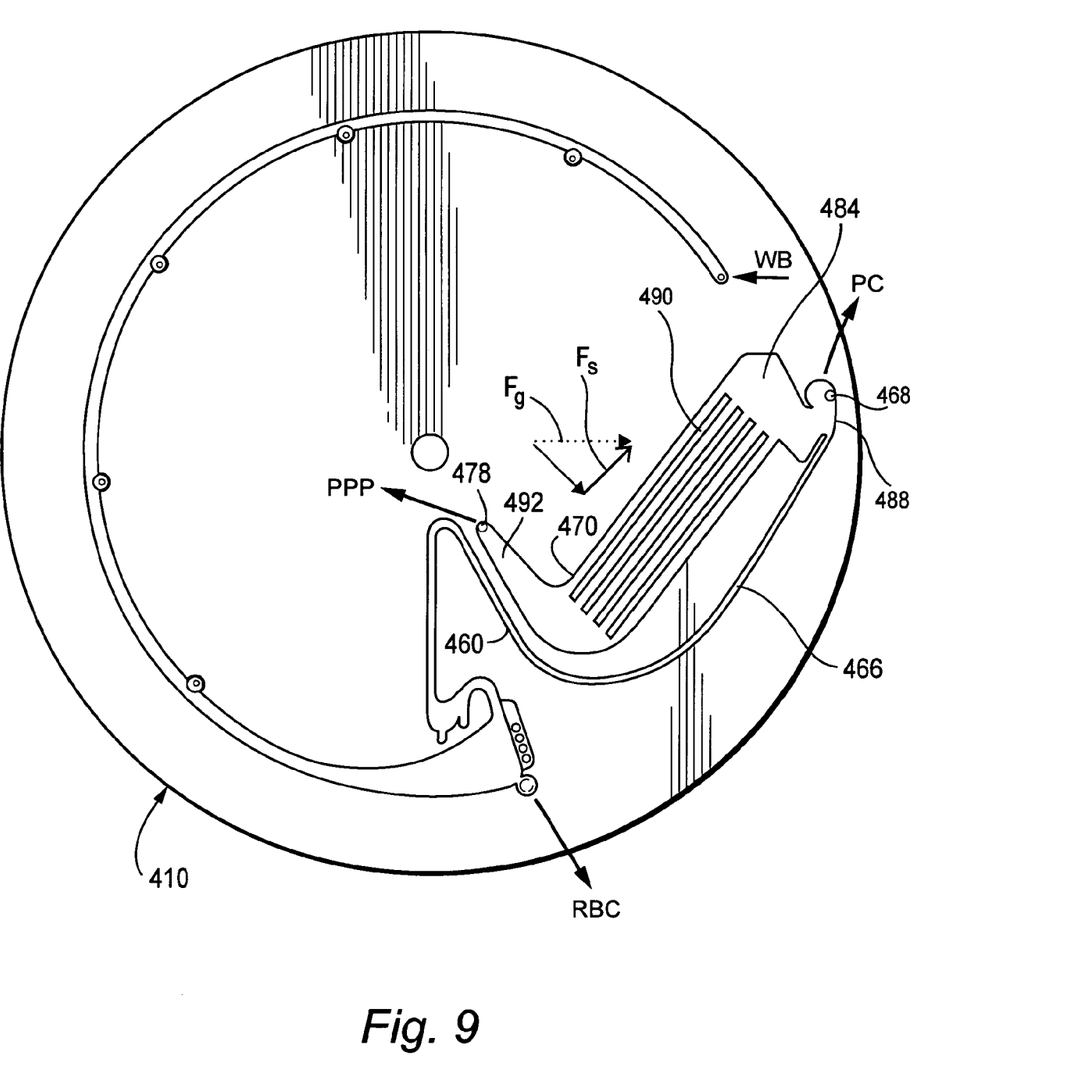
FIG. 9 is a schematic plan view of yet another example embodiment of the invention, including a second stage with multichannel exit.

Yet another example embodiment is shown in FIG. 9, where the platelet rich plasma (PRP) stream flows through channel 466 and continues to the maximum gravitational area 488 just upstream of the port 468 and encounters toroid-shaped segment 484 where it slows down. With platelets at the outer radius and plasma at the inner radius of 484, the incoming flow has to make a sharp turn. This turn in the direction of flow guides those platelets, being slowed down in the larger cross-sectional area of toroid-shaped section 484 and which did not get harvested in the platelet port 468, back in the direction of that port. This increases the probability of the platelet's movement being dominated more by the influence of the centrifugal force, which is pulling and guiding the cells toward platelet (PC) port 468.

When leaving the PC-port area 468 the fluid has lost the majority of the original platelet load, but it is possible to remove even more of the remaining platelets from the fluid, and either bring them back to the PC-port for harvesting, or at least prevent them from contaminating the plasma that is leaving through the platelet poor plasma (PPP) port 478, which per numerous regulatory standards in force has to have minimum platelet count so as to comprise platelet-poor-plasma PPP.

In one embodiment (FIGS. 1 and 4 and also to a lesser degree 6) this is achieved by slowing down the flow in channel 76, 176, 276, which has a significantly enlarged cross-sectional area compared to channel 66, 166, 266. This lower velocity gives the platelets a greater chance to follow the influence of the gravitational force to reach the outer wall 77, 177, 277 of the channel, where they accumulate and start sliding down towards the PC-port, a behaviour observed during tests of exemplary embodiments with human blood. If the distance from the PC-port is sufficiently large, the small amount of platelets remaining in the fluid will, under the continued strong influence of the centrifugal force, find the outer wall of the long channel 76, 176, 276 which the flow has to follow before reaching PPP-port 78, 178, 278 where now clean plasma can be extracted.

In another embodiment, shown in FIG. 9, the long path 470 leading from the PC-port 468 area to the PPP-port 478 has been shortened in length but has been substantially extended in width. A structure of multiple parallel paths (multi-channel) 490 provides for the necessary wall area for the platelets to settle and eventually to slide down towards the PC-port. For this purpose the multi-channel structure is oriented appropriately, e.g., generally parallel to channel 466 with respect to the direction of the centrifugal force Fg providing for a significant sliding component $F_s$ of the centrifugal force Fg under the influence of which the platelets at the wall start moving and sliding toward the PC-port 468.

When the fluid gets closer to the end of the multi-channel structure 490, the direction of the centrifugal force is more square with respect to the multichannel walls, which assures that platelets having escaped up to this point are more effectively pushed towards the nearest wall-area in their vicinity, where they will be kept adhered without the possibility to move on towards the PPP-port 478.

Finally, the last portion of the channel 492 is oriented such that the plasma has to flow radially inwardly, against the direction of the centrifugal force, again making it more difficult for particles to get to the PPP-port 478. Therefore, the plasma being extracted at the PPP-port 478 is substantially free of cells.

In summary, a cell separation chamber is provided comprising at least two separate stages which minimize the detrimental occurrence of spill over and with traps in locations to eliminate the unwanted contaminants, and further combines Coriolis force and gravity in sedimenting and concentrating cells more efficiently. The highly efficient first stage produces maximum concentration of platelets on the top of an RBC of desired hematocrit and the second stage has many features to further concentrate cells (platelets) for effective harvesting and to allow the collection of least contaminated plasma. Each of the components, i.e. RBC, PC, and PRP, can be harvested alone or in combination in line, with a lower whole blood flow requirement from a donor or patient vein thus increasing the possibility of application in a more clean and efficient manner to more donors or patients.

In one example, the flow direction is changed significantly, e.g., making a U-turn, causing platelets to change direction and the sense of momentum giving a higher probability of being captured at the point of highest gravitational force. In addition, platelets moving in opposite directions, that is platelets moving in the direction of flow and platelets moving according to gravitational force, come in contact and adhere to each other, forming configurations of cells leading to a more effective separation and, according to Stokes sedimentation law, since adhered platelets form clusters with less cross-sectional area relative to the volume, and thus, experience less drag force which is opposite in direction to the gravitational force.

In general, the features of the second stage are not limited to separating platelets from plasma. In this regard, the configuration, properly adapted, can be used to serve as a first stage for separating red blood cells from whole blood or to extract stem cells or granulocytes depending on the targeted cell population.

Based on actual experiments with blood using an example embodiment of the above described second stage structure, efficiencies of 90% or better have been achieved in regard to platelet extraction for the second stage. Coupling such a second stage with a first stage according to an example embodiment of the invention would thus yield an approximate 80% overall efficiency of the assembly, which is in marked contrast to current commercial separators which typically have maximum overall efficiencies of no more than 60 to 70%.

While the invention has been described in connection with what is presently considered to be the most practical and preferred embodiment, it is to be understood that the invention is not to be limited to the disclosed embodiments, but on the contrary, is intended to cover various modifications and equivalent arrangements included within the spirit and scope of the appended claims.

What is claimed is:

1. A centrifuge assembly for separating particles of differing density from a fluid mixture of particles comprising:
    a base component disposed for rotation about a central axis thereof and including an inlet for said mixture, a first particle outlet for a first particle type having a first density, a fluid outlet for fluid from which said first particle type has been substantially removed, and a first channel extending from said mixture inlet to said first outlet, said first channel being defined by a radially inner side wall, a radially outer side wall and a channel bottom wall, the radially inner side wall being radially closer than the outer side wall to an axis of rotation of the base component; wherein
    at least a part of said first channel extends in an arc proximate an outer peripheral edge of said base component; and
    a plurality of spaced mixer components disposed to project into said first channel from said radially inner wall of said first channel, so that as said first particles are separated from said mixture while said base component is rotating and as said mixture flows along said first channel, said plurality of mixer components re-mixes at least some of said separated first particles, said radially outer side wall and said channel bottom wall being free from projecting mixer components.

2. A centrifuge assembly as in claim 1, wherein said first channel has a substantially constant radial width along the length thereof from adjacent said mixture inlet to a point proximate said first particle outlet and wherein said first channel substantially radially widens in a vicinity of said first particle outlet, said mixer components being disposed upstream, with respect to a mixture flow direction, of the radial widening of the first channel, so that said mixture components are disposed along the length of the first channel having said substantially constant radial width.

3. A centrifuge assembly as in claim 2, wherein said radially outer wall of said first channel is defined at a substantially constant radius along a length of said substantially an entire length of said channel and wherein said radially inner wall of said first channel diverges radially inwardly adjacent the first particle outlet, thereby to define said widened portion of said first channel.

4. A centrifuge assembly as in claim 2, wherein said mixer components are substantially uniformly spaced along the length of the first channel having said substantially constant radial width.

5. A centrifuge assembly of claim 1, further comprising an optical sensor adjacent said first particle outlet for detecting a position of first particles separated from said mixture adjacent said first particle outlet.

6. A centrifuge assembly as in claim 1, wherein said mixer components are substantially uniformly spaced along a substantial portion of the length of the first channel.

7. A centrifuge assembly for separating at least first and second particle types having different densities from a fluid mixture of at least said first and second particle types suspended in a fluid comprising:
    a base component having a generally circular shape and defining a path for fluid extending generally in a circumferential direction thereof, wherein said path for fluid is defined in first and second part circumferential stages, and further comprising a generally radial passage communicating a second, terminal end of said first stage and a first, beginning end of said second stage, wherein said first end of said second stage is disposed radially inwardly of said second end of said first stage, wherein said generally radial passage comprises a first radially extending portion, a second, part circumferential portion, and a third, radially extending portion, said second portion extending from an upstream end thereof to a downstream end thereof generally parallel to a portion of said first part circumferential stage in a counter flow direction with respect to a flow direction in said first stage, said second portion having a transverse cross-sectional area greater than a transverse cross-sectional area of either of said first and third portions, and wherein said third portion extends radially inwardly from said downstream end of said second portion to said beginning end of said second stage.

8. A centrifuge assembly as in claim 7, wherein said second portion further comprises at least one particle trap recess in a radially outer wall thereof.

9. A centrifuge apparatus for separating particles from a mixture of fluid and at least said particles comprising:
    a generally circular base for being rotated in a first direction about a central axis thereof for generating forces to facilitate separation of said particles from said mixture and a channel extending at least part circumferentially of said base, said channel having an inlet for said mixture, a particle outlet, and a fluid outlet for fluid from which said particles have been substantially removed, said inlet being disposed proximate said center of said base, said channel including a first portion extending radially outwardly from said inlet, a second portion extending part circumferentially of said base proximate an outer periphery of said base to a vicinity of said particle outlet, and a third portion extending at least one of part circumferentially and radially inwardly of said base from a vicinity of said particle outlet to said fluid outlet, wherein said first portion of said channel is constructed and arranged so that particles in said mixture flowing along said first portion experience Coriolis forces for urging said particles towards a downstream outer wall thereof, and said second portion is constructed and arranged such that particles in said mixture flowing along said second portion experience gravitational forces for urging said particles towards a radially outer wall thereof, said particle outlet being disposed along said radially outer wall of said second portion of said channel, upstream of said third portion with respect to a direction of mixture flow through said channel.

10. A centrifuge apparatus as in claim 9, wherein said second portion of said channel has a generally constant radial width along a terminal portion thereof approaching said particle outlet.

11. A centrifuge apparatus as in claim 9, wherein said second portion of said channel has a radial width that gradually increases along a terminal portion thereof approaching said particle outlet.

12. A centrifuge apparatus as in claim 9, wherein said channel includes an abrupt channel expansion adjacent said particle outlet.

13. A centrifuge apparatus as in claim 9, wherein a flow path defined by said channel makes a substantial U-turn in the vicinity of said particle outlet, between said second and third portions.

14. A centrifuge apparatus as in claim 9, wherein said third portion is substantially wider than said second portion.

15. A centrifuge apparatus as in claim 14, wherein said third portion includes a plurality of longitudinal partitions for defining multiple channels therein.

16. A centrifuge apparatus as in claim 14, wherein said third portion is substantially wider than said second portion along substantially an entire length of said third portion.

* * * * *